United States Patent
Mohl et al.

(10) Patent No.: US 11,717,302 B2
(45) Date of Patent: *Aug. 8, 2023

(54) METHOD AND DEVICE FOR THE INTERMITTENT OCCLUSION OF THE CORONARY SINUS

(71) Applicant: Miracor Medical SA, Awans (BE)

(72) Inventors: Werner Mohl, Altenmarkt-Thenneberg (AT); Loay Alzubaidi, Saar (BH)

(73) Assignee: Miracor Medical Systems GmbH

( * ) Notice: Subject to any disclaimer, the term of this patent is extended or adjusted under 35 U.S.C. 154(b) by 321 days.

This patent is subject to a terminal disclaimer.

(21) Appl. No.: 16/859,475

(22) Filed: Apr. 27, 2020

(65) Prior Publication Data

US 2020/0268391 A1    Aug. 27, 2020

Related U.S. Application Data

(63) Continuation of application No. 15/637,072, filed on Jun. 29, 2017, now Pat. No. 10,667,820, which is a (Continued)

(30) Foreign Application Priority Data

Jun. 8, 2004 (AT) .................... A 993/2004

(51) Int. Cl.
*A61B 17/12* (2006.01)
*A61M 60/295* (2021.01)
(Continued)

(52) U.S. Cl.
CPC .... *A61B 17/1204* (2013.01); *A61B 17/12022* (2013.01); *A61B 17/12122* (2013.01);
(Continued)

(58) Field of Classification Search
CPC .......... A61B 17/1204; A61B 17/12022; A61B 17/12122; A61B 17/12136; A61B 5/021;
(Continued)

(56) References Cited

U.S. PATENT DOCUMENTS

| 1,611,914 A | 12/1926 | Jenkins |
| 3,995,623 A | 12/1976 | Blake et al. |

(Continued)

FOREIGN PATENT DOCUMENTS

| AT | WO03008018 | * 1/2003 | ............. A61M 1/00 |
| EP | 0230996 | 8/1987 | |

(Continued)

OTHER PUBLICATIONS

'Cannulation' [online]. Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>.

(Continued)

*Primary Examiner* — Kathleen S Holwerda
*Assistant Examiner* — Lauren Dubose
(74) *Attorney, Agent, or Firm* — Fish & Richardson P.C.

(57) ABSTRACT

In a method for intermittently occluding the coronary sinus, in which the coronary sinus is occluded using an occlusion device, the fluid pressure in the occluded coronary sinus is continuously measured and stored, the fluid pressure curve is determined as a function of time, and the occlusion of the coronary sinus is triggered and/or released as a function of at least one characteristic value derived from the measured pressure values. The pressure increase and/or pressure decrease per time unit each occurring at a heart beat are used as characteristic values.

20 Claims, 4 Drawing Sheets

Related U.S. Application Data continuation of application No. 14/444,006, filed on Jul. 28, 2014, now Pat. No. 9,724,102, which is a continuation of application No. 13/593,984, filed on Aug. 24, 2012, now Pat. No. 8,790,265, which is a continuation of application No. 12/855,473, filed on Aug. 12, 2010, now Pat. No. 8,262,580, which is a continuation of application No. 11/597,834, filed as application No. PCT/AT2005/000204 on Jun. 7, 2005, now Pat. No. 7,780,604.

(51) Int. Cl.
| | |
|---|---|
| *A61M 60/531* | (2021.01) |
| *A61M 60/857* | (2021.01) |
| *A61M 60/143* | (2021.01) |
| *A61M 60/554* | (2021.01) |
| *A61M 60/497* | (2021.01) |
| *A61B 5/021* | (2006.01) |
| *A61B 17/00* | (2006.01) |
| *A61M 60/422* | (2021.01) |
| *A61M 60/824* | (2021.01) |

(52) U.S. Cl.
CPC ..... *A61B 17/12136* (2013.01); *A61M 60/143* (2021.01); *A61M 60/295* (2021.01); *A61M 60/497* (2021.01); *A61M 60/531* (2021.01); *A61M 60/554* (2021.01); *A61M 60/857* (2021.01); *A61B 5/021* (2013.01); *A61B 2017/00022* (2013.01); *A61M 60/422* (2021.01); *A61M 60/824* (2021.01); *A61M 2205/3344* (2013.01); *A61M 2205/3355* (2013.01)

(58) Field of Classification Search
CPC ............ A61B 2017/00022; A61M 2205/3344; A61M 2205/3355; A61M 60/143; A61M 60/497; A61M 60/531; A61M 60/554
See application file for complete search history.

(56) References Cited

U.S. PATENT DOCUMENTS

| | | | |
|---|---|---|---|
| 4,589,869 | A | 5/1986 | Wernborg |
| 4,657,536 | A | 4/1987 | Dorman |
| 4,670,009 | A | 6/1987 | Bullock |
| 4,671,796 | A | 6/1987 | Groshong et al. |
| 4,701,166 | A | 10/1987 | Groshong et al. |
| 4,705,501 | A | 11/1987 | Wigness et al. |
| 4,887,608 | A | 12/1989 | Mohl et al. |
| 4,931,036 | A | 6/1990 | Kanai et al. |
| 4,934,996 | A | 6/1990 | Mohl et al. |
| 4,943,277 | A | 7/1990 | Bolling |
| 4,969,470 | A | 12/1990 | Mohl et al. |
| 5,021,045 | A | 6/1991 | Buckberg et al. |
| 5,024,668 | A | 6/1991 | Peters et al. |
| 5,156,600 | A | 10/1992 | Young |
| 5,224,938 | A | 7/1993 | Fenton, Jr. |
| 5,226,427 | A | 7/1993 | Buckberg et al. |
| 5,324,260 | A | 6/1994 | O'Neill et al. |
| 5,456,665 | A | 10/1995 | Postell et al. |
| 5,458,574 | A | 10/1995 | Machold et al. |
| 5,466,216 | A | 11/1995 | Brown et al. |
| 5,505,698 | A | 4/1996 | Booth et al. |
| 5,683,347 | A | 11/1997 | Miyata et al. |
| 5,707,358 | A | 1/1998 | Wright |
| 5,779,685 | A | 1/1998 | Thompson et al. |
| 5,755,686 | A | 5/1998 | O'Neill et al. |
| 5,775,327 | A | 7/1998 | Randolph et al. |
| 6,029,671 | A | 2/2000 | Stevens et al. |
| 6,179,856 | B1 | 1/2001 | Barbere |
| 6,475,209 | B1 | 11/2002 | Larson et al. |
| 6,500,145 | B1 | 12/2002 | Bicakci et al. |
| 6,506,146 | B1 | 1/2003 | Mohl et al. |
| 6,508,777 | B1 | 1/2003 | Macoviak et al. |
| 6,569,145 | B1 | 5/2003 | Shmulewitz et al. |
| 6,673,040 | B1 | 1/2004 | Samson et al. |
| 6,758,854 | B1 | 7/2004 | Butler et al. |
| 7,166,100 | B2 | 1/2007 | Jordan et al. |
| 7,331,922 | B2 | 2/2008 | Mohl et al. |
| 7,780,604 | B2 | 8/2010 | Mohl et al. |
| 8,262,580 | B2 | 9/2012 | Mohl et al. |
| 8,790,265 | B2 | 7/2014 | Mohl et al. |
| 9,724,102 | B2 | 8/2017 | Mohl et al. |
| 10,667,820 | B2 | 6/2020 | Mohl et al. |
| 2001/0053920 | A1 | 12/2001 | Shaker |
| 2002/0072730 | A1 | 6/2002 | McGill et al. |
| 2002/0120232 | A1 | 8/2002 | Stumpp et al. |
| 2003/0032974 | A1 | 2/2003 | Leschinsky et al. |
| 2004/0172004 | A1* | 9/2004 | Mohl ................. A61M 1/3613 604/509 |
| 2005/0015048 | A1* | 1/2005 | Chiu ................... A61M 25/10 604/101.04 |
| 2006/0074399 | A1 | 4/2006 | Bates |
| 2007/0083126 | A1 | 4/2007 | Marko et al. |
| 2008/0015404 | A1 | 1/2008 | Mohl |
| 2008/0119742 | A1 | 5/2008 | Mohl |
| 2010/0056849 | A1 | 3/2010 | Mohl |
| 2010/0130810 | A1 | 5/2010 | Mohl |

FOREIGN PATENT DOCUMENTS

| | | |
|---|---|---|
| EP | 1611914 | 1/2006 |
| UA | 14911 U | 6/2006 |
| WO | WO 1989010155 | 11/1989 |
| WO | WO 2003008018 | 1/2003 |
| WO | WO 2003041783 | 5/2003 |

OTHER PUBLICATIONS

'Cardioplegia Delivery' [online]. Quest Medical, Inc. 2010 [retrieved May 27, 2010]. Retrieved from the Internet: <URL: http://www.questmedical.com/products/cardio_catheters.asp>.

'Global Myocardial Protection' [online]. Edwards Lifesciences, 2004 [retrieved May 27, 2010]. Retrieved from the Internet: <URL: http://ht.edwards.com/resourcegallery/products/cannulae/images/ar00519.pdf>.

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010], Retrieved from the Internet: <URL: http://www.anesthesia-analgesia.org/content/97/1/298.full.pdf>.

'MiRCSP Cannulae' [online], Medtronic, Inc. 2010 [retrieved May 27, 2010], Retrieved from the Internet: <URL: http://www.medtronic.com/for-healthcare-professionals/products-therapies/cardiovascular/cannulae-products/mircsp-cannula/index.htm>.

'Myocardial Protection System' [online]. Quest Medical, Inc. 2010 [retrieved May 27, 2010]. Retrieved from the Internet: <URL: http://www.questmedical.com/products/mps.asp>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

'Retrograde Perfusion Cannulae' [online], Medtronic, Inc. 2010 [retrieved May 27, 2010], Retrieved from the Internet: <URL: http://www.medtronic.com/for-healthcare-professionals/products-therapies/cardiovascular/cannulae-products/retrograde-perfusion-cannulae/index.htm>.

International Search Report for PCT/AT2005/000204 dated Aug. 24, 2005, 6 pages.

Mohl et al., "Intermittent pressure elevation of the coronary venous system as a method to protect ischemic myocardium," Interact CardioVac Thorac Surg., 2005, 4:66-69.

Mohl, Werner et al. "Coronary Sinus Library, ICSO and PICSO" Society of Coronary Sinus Interventions, 2003. A. Holzhausens Nfg., Austria.

(56) References Cited

OTHER PUBLICATIONS

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

Syeda et al., "The salvage potential of coronary sinus interventions: Meta-analysis and pathophysiologic consequences," J Thorac Cardiovasc Surg., 2004, 124:1703-1712.

* cited by examiner

METHOD AND DEVICE FOR THE INTERMITTENT OCCLUSION OF THE CORONARY SINUS

CROSS-REFERENCE TO RELATED APPLICATIONS

This application is a continuation of U.S. application Ser. No. 15/637,072 filed Jun. 29, 2017, which is a continuation of U.S. application Ser. No. 14/444,006 filed Jul. 28, 2014, which is a continuation of U.S. application Ser. No. 13/593,984 filed on Aug. 24, 2012, which is a continuation of U.S. application Ser. No. 12/855,473 filed on Aug. 12, 2010, which is a continuation of U.S. application Ser. No. 11/597,834 filed on Nov. 28, 2006, which is a U.S. national phase of PCT application PCT/AT2005/000204 filed on Jun. 7, 2005, which claims priority to Austrian patent application no. AT A 993/2004 filed on Jun. 8, 2004, the entire contents of each of which are hereby incorporated by reference.

TECHNICAL FIELD

The invention relates to a method for intermittently occluding the coronary sinus, in which the coronary sinus is occluded using an occlusion device, the fluid pressure in the occluded coronary sinus is continuously measured and stored, the fluid pressure curve is determined as a function of time, and the occlusion of the coronary sinus is triggered and/or released as a function of at least one characteristic value derived from the measured pressure values, as well as a device for the intermittent occlusion of the coronary sinus.

BACKGROUND

Arterial blood, which supplies the heart muscle, is able to pass through healthy heart tissue while nourishing the same, yet has difficulty reaching ischemic tissue. As a result, the supply of ischemic tissue with nutrients and the discharge of metabolic catabolites from such ischemic tissue will be impaired.

In this context, it has already been proposed to supply ischemic tissue with blood through retrograde perfusion. This means that blood is tried to be allowed to flow back from the coronary sinus through the coronary venous system in counterflow by feeding blood from a different source into the coronary sinus, either by permanently connecting an artery with the coronary sinus or by temporarily inserting a catheter into the sinus, which catheter is supplied with blood taken from a remote artery and transported by the aid of a blood pump located outside the patient's body.

Another technique proposed for retroperfusion uses an inflatable balloon which is fixed to the end of a catheter to intermittently occlude the coronary sinus. The blood pressure in the coronary sinus rises during the occlusion at every heart beat so as to cause blood reaching the coronary sinus through the healthy tissue of the heart muscle to be flushed back into the ischemic tissue. For such an intermittent coronary sinus occlusion, the balloon end of the catheter is inserted either percutaneously or surgically. The other end of the catheter is supplied with a gas or fluid by a pump which causes the cyclic inflation and deflation of the balloon.

A typical application of blood retroinfusion in coronary veins through intermittent coronary sinus occlusion applies to myocardial protection during a short-term coronary arterial occlusion in the context of a cardiologic intervention. A typical such intervention comprises, for instance, the balloon dilatation of an arteriosclerotically constricted coronary artery. That method, which is also known as percutaneous transluminal coronary angioplasty (PTCA), comprises the conduction of a balloon catheter into the region of the coronary artery stenosis under X-ray control and the compression of the osclerotic plaque by the inflation of the balloon, which is located on the end of the catheter. During the dilatation of the balloon, no supply of the tissue with oxygen-containing blood takes place downstream in the artery with functional changes in the ischemic area of the myocard being detectable already at dilatations lasting longer than 30 seconds. Consequential problems of the ischemic protection of the myocard will also be faced with other interventions aimed at coronary vascularization such as, e.g., atherectomy, coronary endoprostheses and laser applications.

A device for the retroinfusion of coronary veins is, for instance, known from U.S. Pat. No. 4,934,996, by which a pressure-controlled, intermittent coronary sinus occlusion can be performed. The device comprises a means for occluding the sinus such as, e.g., an inflatable balloon catheter, a pressure measuring unit for measuring the fluid pressure within the coronary sinus and a control unit which generates triggering signals for the occlusion device to trigger or release an occlusion. The control unit is devised in a manner that the pressure maximum in the coronary sinus is measured during every heart beat, a plateau value of the pressure maxima of consecutive heart beats is estimated by calculation and the occlusion of the coronary sinus is released on the basis of the plateau value of the pressure maxima.

The occlusion of the coronary sinus causes a pressure increase and, as a result, a retroperfusion of blood via the respective vein into the nutritive capillaries of the ischemic area so as to enable the supply of nutrients to that area. At a release of the occlusion, the retroperfused blood is flushed out while the metabolic waste products are carried off at the same time. In the method according to U.S. Pat. No. 4,934,996, a systolic pressure curve is, thus, estimated based on the measurement of the pressure maximum in the coronary sinus during every heart beat, with the intermittent occlusion being controlled as a function of the plateau value of the systolic pressure curve. The course of the estimated systolic pressure curve also allows for a conclusion as to the efficiency of the heart, with the slope of the curve reflecting, for instance, the contractibility of the heart.

Under certain circumstances, the determination of the moment of release of the occlusion by way of plateau values of the systolic pressure curve according to U.S. Pat. No. 4,934,996 is, however, not feasible with sufficient accuracy.

SUMMARY

The present invention, therefore, aims to propose a method and device for the intermittent occlusion of the coronary sinus, in which characteristic values are used to control the occlusion, which permit the determination of the precise time at which the occlusion of the coronary sinus is to be released or triggered. At the same time, it is to be ensured that the time of release, or the time of triggering, of the occlusion is selected with a view to optimizing therapeutic and/or diagnostic effects while preventing an impairment of the heart muscle.

To solve this object, the method according to the invention essentially consists in that the pressure increase and/or pressure decrease per time unit each occurring at a heart beat is used as said characteristic value. The respective device according to the invention includes an occlusion device, a pressure measuring device for continuously measuring the fluid pressure in the occluded coronary sinus, and a memory for storing the fluid pressure curve as a function of time, and is characterized in that an evaluation circuit is provided for the determination of the pressure increase and/or pressure decrease per time unit each occurring at a heart beat, which cooperates with the occlusion device to trigger and/or release the occlusion of the coronary sinus. The pressure increase or pressure decrease per time unit each reflects the positive or negative gradient of the fluid pressure curve to be observed within a heart beat and, departing from the fluid pressure curve, is calculated as a function of time and the pressure increase or pressure decrease ($\Delta p$) readable from this function within a time interval ($\Delta t$) as follows: ($\Delta p$)/($\Delta t$). This characteristic value enables the attending physician to make conclusions as to the contractibility of the heart and the conditions within the coronary sinus both during the occlusion of the coronary sinus (occlusion phase) and also after the release of the occlusion (release phase), in order to deduce therefrom the optimum occlusions times. To this end, it is surprisingly not necessary to know the pressure prevailing within the coronary sinus in absolute numbers, but it will do according to the invention to evaluate pressure differences, i.e. the pressure increase or pressure decrease respectively occurring per time unit within a heart beat.

The pressure curve in the occluded coronary sinus, as a rule, extends in a manner that the speed of the pressure increase rises with every heart beat and, hence, ever increasing systolic pressure peaks will occur until a so-called "plateau phase" will have been reached, in which the speed of the pressure increase will further rise at consecutive heart beats, yet the systolic pressure will already have attained a plateau value, thus remaining substantially constant. It is only when the contractibility of the heart decreases in this plateau phase by arterial underperfusion (coronary resistance increase) that the speed of the pressure increase will drop again, with the systolic pressure substantially continuing to remain on the plateau value. If, as in accordance with the present invention and deviating from the prior art, the determination of the optimum time of release of the occlusion is not based on absolute pressure values such as, for instance, the plateau value of the systolic pressure peaks, but on the speed of the pressure increase, it will be feasible to maintain the occlusion over an extended period of time without affecting the heart. It is, in fact, possible to only release the occlusion at a time at which the speed of the pressure increase during consecutive heart beats has attained a maximum, or at a time at which a predetermined percentage of the calculated or estimated maximum of the speed of the pressure increase has been reached, which time is after the achievement of the systolic plateau value. The fact that the occlusion can be maintained over an extended period of time without overstressing or affecting the heart or heart vessels advantageously results in an augmented release of angiopoietic genes (VEGF genes, vascular endothelial growth factor encoding genes) due to the pressure increase lasting as long as possible, which will also be beneficial to the regeneration of the vessels.

The control of the release or triggering of the occlusion as a function of the pressure increase or pressure decrease, respectively, per time unit may be realized in various ways. The occlusion might, for instance, be released as soon as a predetermined upper limit value for the characteristic value $\Delta p/\Delta t$ has been exceeded or, vice versa, might be triggered as the characteristic value $\Delta p/\Delta t$ is falling short of a lower limit value. According to a preferred method variant, it is, however, proceeded according to the invention in a manner that the pressure increase per time unit occurring at a heart beat is determined and the occlusion of the coronary sinus is released after the pressure increase per time unit of consecutive heart beats has attained a maximum, wherein the respective device in this case is devised such that the evaluation circuit is configured to determine the pressure increase per time unit each occurring at a heart beat, and cooperates with the occlusion device in a manner that the occlusion of the coronary sinus is released after the pressure increase per time unit of consecutive heart beats has reached a maximum. This ensures the precise determination of the optimum length of the occlusion time. For the period of the release phase, it may analogously be proceeded in a manner that the pressure decrease per time unit occurring at a heart beat is determined and the occlusion is triggered after the pressure decrease per time unit of consecutive heart beats has reached a minimum.

A further refinement of the method, which is particularly easy to realize using a mathematical algorithm, is feasible for the occlusion phase in that the first derivative of the fluid pressure is calculated with respect to time, that the local maximum each occurring within a heart beat, of the first derivative is determined, and that the occlusion of the coronary sinus is released after the local maxima of consecutive heart beats have reached a maximum. For the release phase, it is analogously provided in a preferred manner that the first derivative of the fluid pressure is calculated with respect to time, that the local minimum each occurring within a heart beat, of the first derivative is determined, and that the occlusion of the coronary sinus is triggered after the local minima of consecutive heart beats have reached a minimum.

For the implementation of this preferred method, the device according to the invention is advantageously further developed in that the evaluation circuit is configured to determine the first derivative of the fluid pressure with respect to time as well as the local maximum of the first derivative each occurring within a heart beat, and cooperates with the occlusion device in a manner that the occlusion of the coronary sinus is released after the local maxima of consecutive heart beats have reached a maximum. In an analogous manner, a configuration is advantageously provided for the release phase, in which the evaluation circuit is configured to determine the first derivative of the fluid pressure with respect to time as well as the local minimum of the first derivative each occurring within a heart beat, and cooperates with the occlusion device in a manner that the occlusion of the coronary sinus is triggered after the local minima of consecutive heart beats have reached a minimum.

DESCRIPTION OF DRAWINGS

In the following, the invention will be explained in more detail by way of an exemplary embodiment illustrated in the drawings. Therein.

DESCRIPTION

Figure 1:
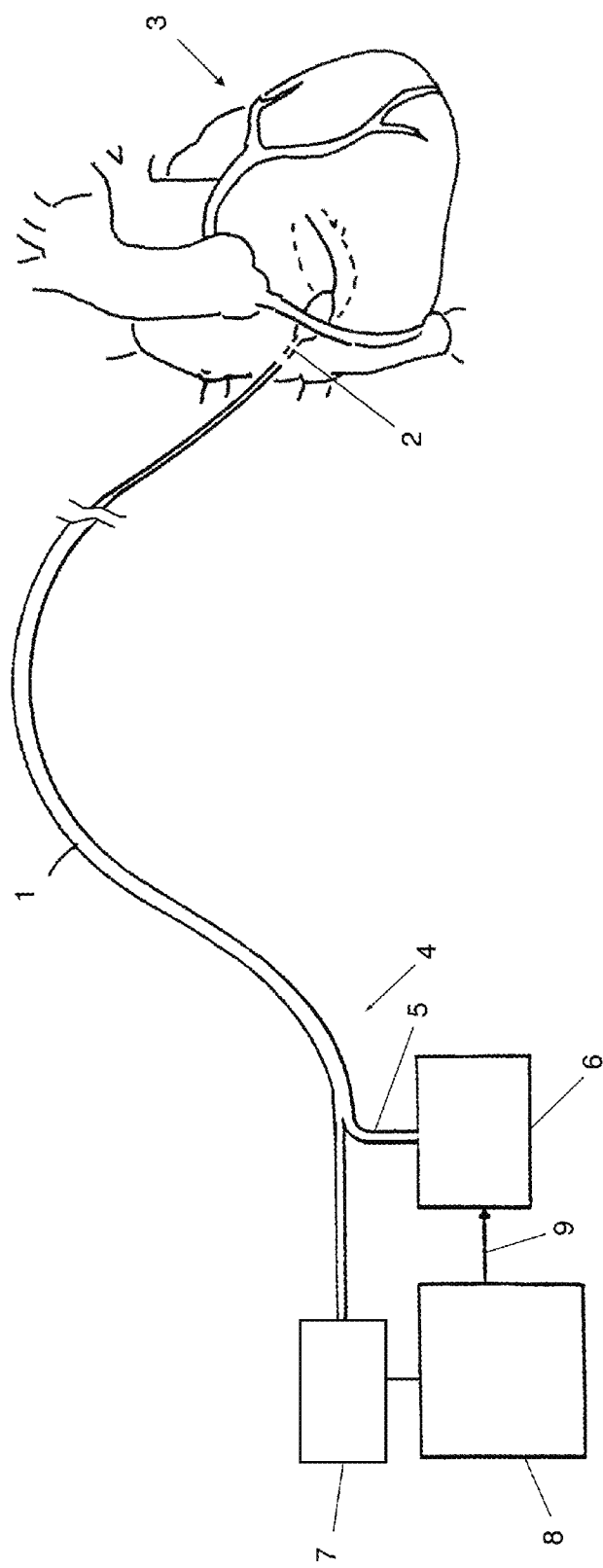
FIG. 1 is a diagrammatic view of a heart including a device for the intermittent occlusion of the coronary sinus.

FIG. 1 schematically depicts the device for the intermittent occlusion of the coronary sinus with a multilumen catheter 1 being apparent, whose distal end 2 is inserted in the coronary sinus of the heart 3 via the atrium. The proximal end 4 of the catheter 1 has a balloon inflation lumen 5 connected with a pump 6. The pressure prevailing on the distal end 2 of the catheter 1 is detected by a pressure measuring device 7, the latter also including a memory for the measured values acquired. The respectively measured pressure values are fed to a control device via an evaluation circuit 8 in order to deliver control signals via line 9 for the start and stop of the pump 6.

Figure 2A:
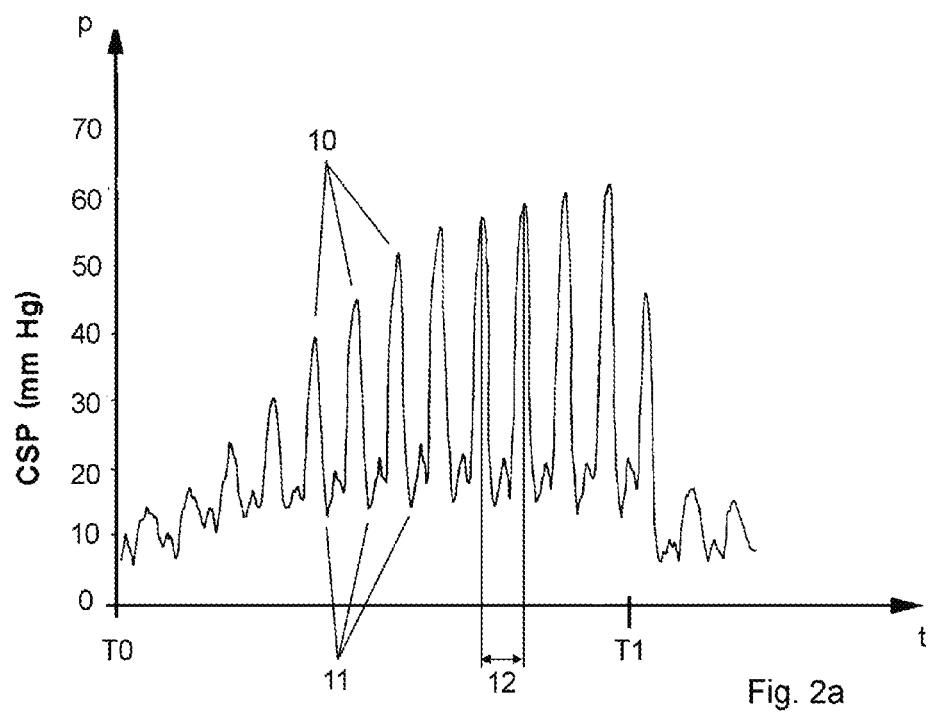
FIGS. 2a-2b are graphical representations of the coronary sinus pressure curve.
Figure 2B:
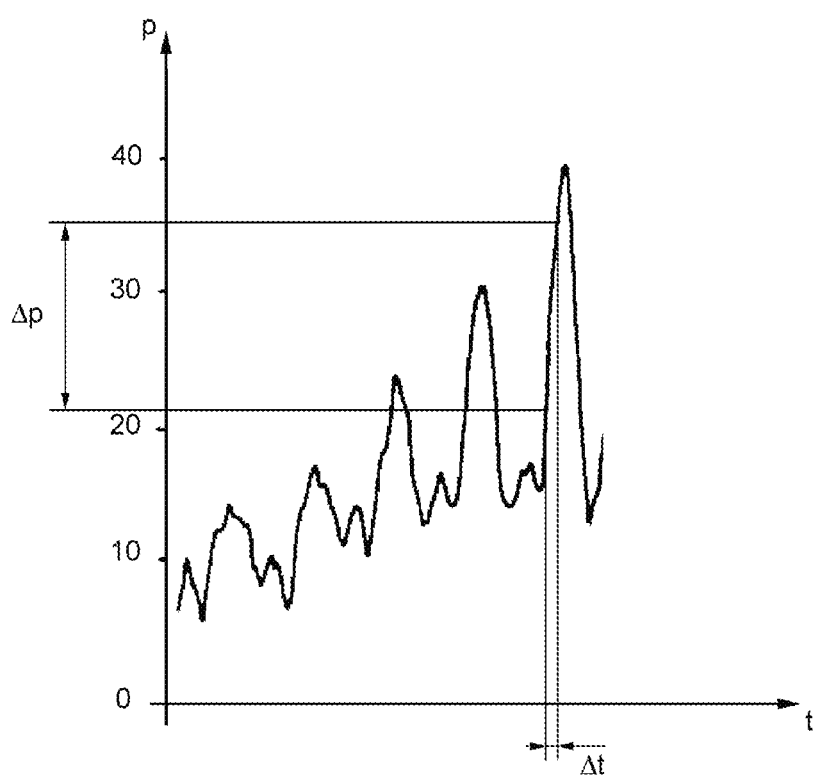
Figure 3:
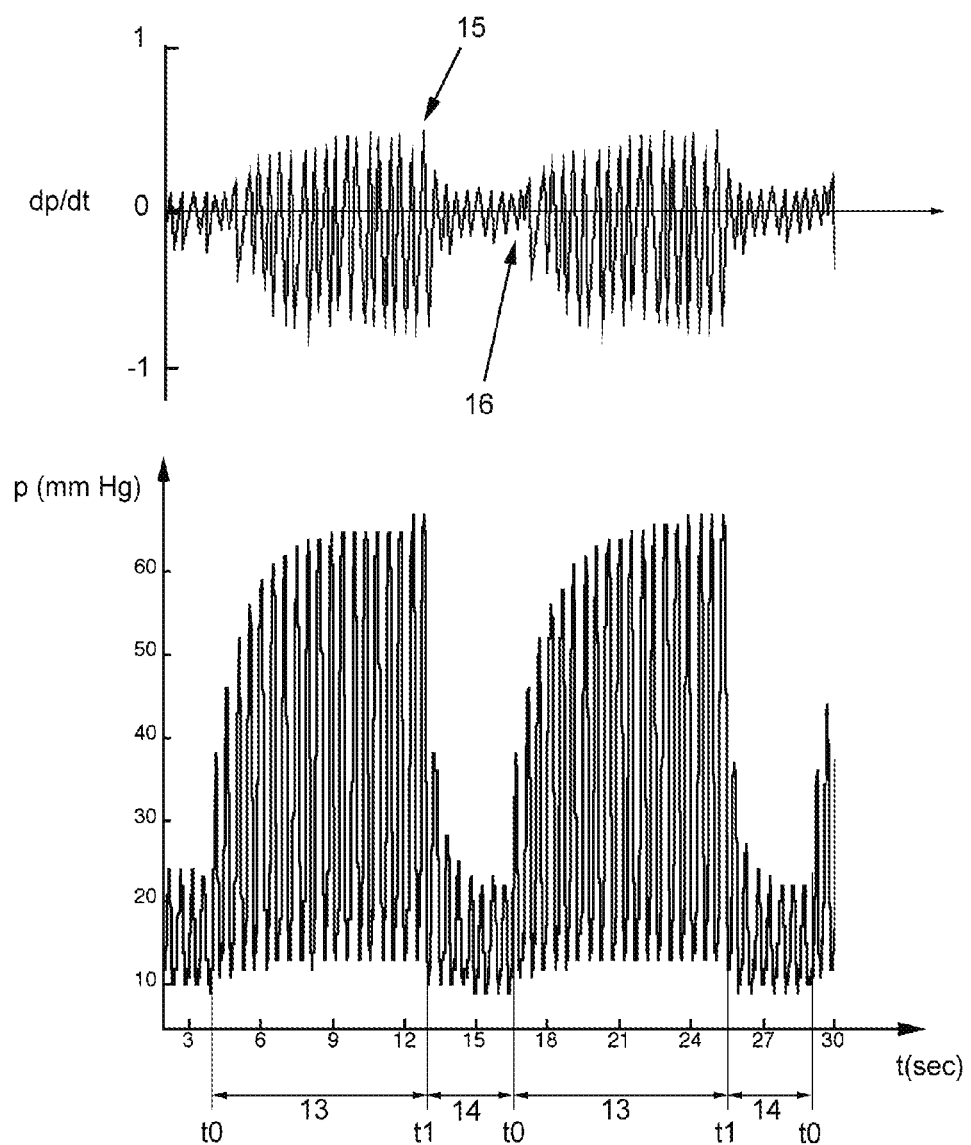
FIG. 3 compares the pressure curve and the derivative of the pressure curve with respect to time.
Figure 4:
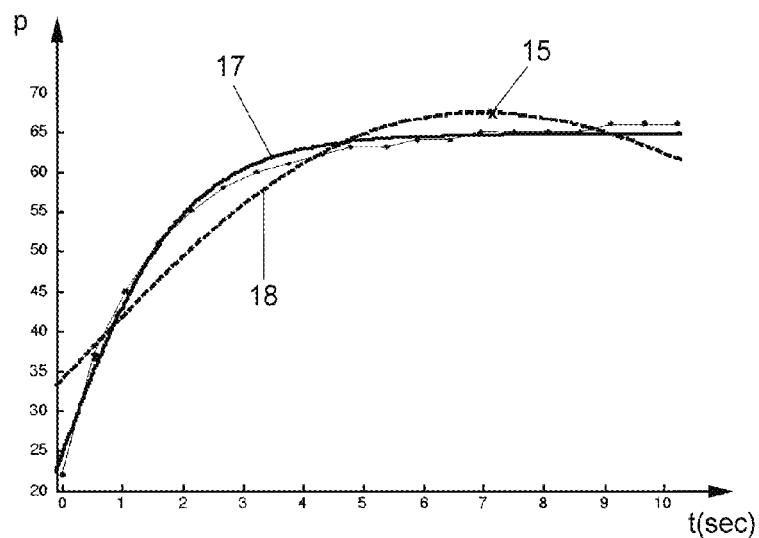
FIG. 4 illustrates the envelopes of the pressure curves according to FIG. 3.

FIG. 2a illustrates the pressure curve determineed by the measuring device 7, with the beginning of the occlusion being shown at T0 and the end of the occlusion being shown at T1. A number of systolic pressure peaks 20 and a number of diastolic valleys 11 are to be seen. The pulse period 12 of the heart beat is represented by the time between consecutive peaks or consecutive valleys. During each heart beat within the occlusion phase 13, the speed of the pressure increase is determined by the calculation of the ratio $\Delta p/\Delta t$ as is schematically illustrated in the enlarged illustration of FIG. 2b. Something analogous occurs in the release phase 14 with the speed of the pressure decrease. For a time interval $\Delta t$ striving to zero, the calculation of a limit value results in an illustration according to FIG. 3, in which the pressure curve is compared to the respective curve of the first derivative $dp/dt$ of the pressure curve. It is apparent that the first derivative reaches a maximum in those points where the slope of the pressure curve is the largest within each heart beat. Similarly, it is apparent that the first derivative reaches a minimum in those points where the negative slope of the pressure curve is the smallest within each heart beat. Since, in the following, only the respective pressure maxima or pressure minima, respectively, occurring within a heart beat as well as the maxima and minima, respectively, of the first derivative of the pressure curve to be observed within each heart beat are of relevance, only the respective envelope curves connecting the respective maxima are illustrated in FIG. 4 for the sake of clarity. FIG. 4, thus, merely exemplifies the envelope curve for the phase of occlusion.

During the occlusion of the coronary sinus it is to be observed that the speed of the pressure increase rises continuously at consecutive heart beats, as is apparent from the envelope curve 17 of the first derivative. The optimum time for a release of the occlusion is in that point 15 in which the envelope curve 17 reaches its maximum, i.e., in which the speed of the pressure increase of consecutive heart beats is the highest. This time can be mathematically determined in the simplest way by equalling the second derivative of the pressure curve to zero. Hence results that a maximum is reached in point 15 of the envelope curve 17 of the first derivative of the pressure curve, whereas the envelope curve 18 connecting the systolic pressure peaks has already previously reached a plateau value. In an analogous manner, the optimum time for the triggering of the occlusion results to be in point 16 (FIG. 3).

By releasing the occlusion in point 15, it is, on the one hand, ensured that the occlusion will be maintained as long as possible such that a pressure level promoting the release of VEGF genes will prevail in the occluded coronary sinus as long as possible. On the other hand, harmful side-effects by too long an occlusion will be avoided, since the occlusion is released in time, namely as soon as the heart's contractibility declines.

To sum up, the present invention provides a method that is simple to perform and a device that is based on an algorithms simple to realize, thus rendering feasible the optimum and precise determination of both occlusion times and release times.

The invention claimed is:

1. A system for intermittently occluding a coronary sinus in a heart, comprising:
    a multi-lumen coronary sinus occlusion catheter including:
        means for occluding a coronary sinus positioned along a distal end of the catheter, and
        means for fluidly communicating with the means for occluding to controllably expand and collapse the means for occluding within the coronary sinus;
    a pressure sensor connected to the multi-lumen coronary sinus occlusion catheter so as to measure a coronary sinus pressure while the means for occluding is expanded in the coronary sinus; and
    a controller that, in response to a comparison of a threshold value to a calculated value including a change in coronary sinus pressure per time unit while the means for occluding is expanded in the coronary sinus, causes the means for occluding to collapse and thereby release of an occlusion of the coronary sinus.

2. The system of claim 1, wherein the pressure sensor is configured to measure a fluid pressure in the coronary sinus at the distal end of the catheter when the means for occluding is expanded in the coronary sinus, and the controller is configured to determine a pressure increase and/or pressure decrease per time unit while the means for occluding is expanded in the coronary sinus.

3. The system of claim 1, wherein the pressure sensor is in communication with a memory that stores data indicative of a fluid pressure curve as a function of time based at least in part on a measured fluid pressure in the occluded coronary sinus when the means for occluding is expanded in the coronary sinus.

4. The system of claim 3, wherein the controller is configured to determine a first derivative of the fluid pressure curve based at least in part on the data stored in the memory that is indicative of a coronary sinus pressure curve as a function of time.

5. The system of claim 1, wherein the means for occluding the coronary sinus comprises an inflatable balloon.

6. The system of claim 1, wherein the means for fluidly communicating comprises a balloon inflation lumen.

7. The system of claim 6, wherein the balloon inflation lumen is connectable to a pump.

8. The system of claim 7, wherein the controller is configured to deliver control signals to the pump while the pump is connected to the balloon inflation lumen.

9. The system of claim 1, wherein the controller is configured to determine a coronary sinus pressure increase per time unit occurring at consecutive heart beats and to cooperate with the means for occluding so as to release the occlusion of the coronary sinus based at least in part on the coronary sinus pressure increase per time unit occurring at consecutive heart beats.

10. The system of claim 1, wherein the pressure sensor measures systolic pressure peaks occurring at consecutive heart beats while the means for occluding is expanded in the coronary sinus.

11. The system of claim 10, wherein the pressure sensor measures diastolic pressure valleys in the coronary sinus occurring between the systolic pressure peaks.

12. The system of claim 9, wherein the determined coronary sinus pressure increase per time corresponds to a maximum coronary sinus pressure increase per time.

13. A system for intermittently occluding a portion of a coronary venous system in a heart, comprising:
a coronary occlusion catheter including:
means for occluding the portion of the coronary venous system positioned along a distal end of the catheter, and
means for fluidly communicating with the means for occluding to controllably expand and collapse the means for occluding within the portion of the coronary venous system;
a pressure sensor connected to the coronary occlusion catheter so as to measure a pressure at the portion of the coronary venous system while the means for occluding is expanded in the portion of the coronary venous system; and
a controller that, in response to a comparison of a threshold value to a calculated value including a change in pressure per time unit while the means for occluding is expanded in the portion of the coronary venous system, causes the means for occluding to collapse and thereby release of an occlusion of the portion of the coronary venous system.

14. The system of claim 13, wherein the pressure sensor is configured to measure a fluid pressure in the portion of the coronary venous system at the distal end of the catheter when the means for occluding is expanded in the portion of the coronary venous system, and the controller is configured to determine a pressure increase and/or pressure decrease per time unit while the means for occluding is expanded in the portion of the coronary venous system.

15. The system of claim 13, wherein the pressure sensor is in communication with a memory that stores data indicative of a fluid pressure curve as a function of time based at least in part on a measured fluid pressure in the occluded portion of the coronary venous system when the means for occluding is expanded in the portion of the coronary venous system.

16. The system of claim 15, wherein the controller is configured to determine a first derivative of the fluid pressure curve based at least in part on the data stored in the memory that is indicative of a pressure curve as a function of time.

17. The system of claim 13, wherein the means for occluding the portion of the coronary venous system comprises an inflatable balloon.

18. The system of claim 13, wherein the means for fluidly communicating comprises a balloon inflation lumen.

19. The system of claim 18, wherein the balloon inflation lumen is connectable to a pump.

20. The system of claim 19, wherein the controller is configured to deliver control signals to the pump while the pump is connected to the balloon inflation lumen.

* * * * *